United States Patent [19]

Plotkin et al.

[11] Patent Number: 4,496,539

[45] Date of Patent: Jan. 29, 1985

[54] METHOD FOR TREATING CANCER USING GALACTOSE-SPECIFIC LECTINS

[75] Inventors: George M. Plotkin, Lynn, Mass.; Charles J. Bendrick, Liverpool, N.Y.; George Wolf, Lexington, Mass.

[73] Assignee: Massachusetts Institute of Technology, Cambridge, Mass.

[21] Appl. No.: 344,497

[22] Filed: Feb. 1, 1982

[51] Int. Cl.$^3$ ................. A61K 37/48; A61K 35/78
[52] U.S. Cl. ................................ 424/94; 424/195
[58] Field of Search ............... 424/94, 195; 435/189

[56] References Cited

U.S. PATENT DOCUMENTS 4,132,600  1/1979  Plotkin et al. .................... 435/15

OTHER PUBLICATIONS

Gontas et al.–J. of Cell Biology, vol. 52 (2 part 1) 1973, pp. 436–443.
Robbins et al.–Chem. Abst., vol. 87 (1977), p. 47981g.
Saltvedt–Chem. Abst., vol. 86 (1977), p. 38388w.
Glimelius et al.–Int. J. Cancer, vol. 14 (1974), pp. 314–325.
Kaneko et al.–Biochem. & Biophys. Res. Comm., vol. 50, No. 4 (1973), pp. 1087–1094.
Nicolson–Symposium Biol. & Chem. Eucaryot. Cell Surface, (1974), pp. 103–124.
Schlepper-Schafer–European J. of Cell Biology, vol. 25 (1981), pp. 95–102.
Onozaki et al.–Biochem. & Biophysical Res. Comm., vol. 48, No. 4 (1972), pp. 783–788.
Nicolson et al.–Chem. Abst., vol. 91 (1979), p. 89400e.
Dodeur et al.–Chem. Abst., vol. 92 (1980), p. 191,157p.

*Primary Examiner*—Sam Rosen
*Attorney, Agent, or Firm*—Arthur A. Smith, Jr.; David E. Brook

[57] ABSTRACT

This invention discloses a method of using galactose-binding lectins, such as Ricinus communis agglutinin I ($RCA_I$), to kill cancer cells. $RCA_I$ has been found to severely weaken certain types of cancer cells, such as bladder carcinoma. This weakening can kill substantial numbers of cancer cells. In addition, it is possible to attach $RCA_I$ to other substances which impose stress on cells, such as cytotoxic drugs or enzymes that catalyze exothermic reactions, which can kill weakened cancer cells.

8 Claims, No Drawings

METHOD FOR TREATING CANCER USING GALACTOSE-SPECIFIC LECTINS

DESCRIPTION

1. Technical Field

This invention is in the fields of biochemistry, pharmacology, and medicine.

2. Background Art

A lectin is a type of substance, normally derived from a plant, that binds with high specificity and affinity to a saccharide ring with a specific configuration [1]. It is believed that lectins may serve as biochemical defense mechanisms within plants, which do not have antibodies, lymphocytes, or other immunological substances that are characteristic of animals. By using a lectin, a plant may be able to immobilize a fungus or other invasive substance. Certain lectins are very toxic to animals and humans.

*Ricinus communis*, commonly known as the castor plant, produces at least two lectins. Ricinus communis agglutinin I ($RCA_I$ also referred to as $RCA_{120}$) binds to galactose. $RCA_{II}$ binds to galactosamine. Both of these lectins are commercially available, either in pure form or conjugated with other substances such as biotin, a B vitamin.

Galactose is a saccharide ring with either of the following structures:

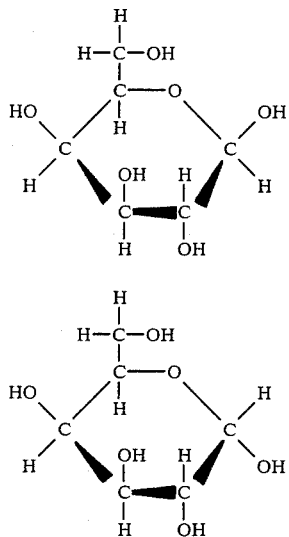

A galactose ring may be conjugated to another molecule through either an "α" or a "β" configuration, indicated as follows:

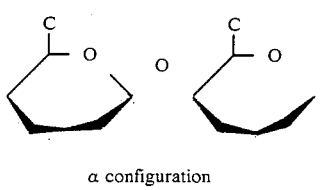

α configuration

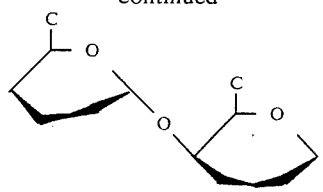

β configuration $RCA_I$ has an affinity for β-galactose conjugates. Other lectins such as Bandeiraea simplicifolia lectin I ($BSL_I$) have affinities for α-galactose conjugates.

Certain types of cancerous cells contain abnormally high amounts of the enzyme galactosyl transferase [2]. This characteristic serves as the basis for at least one method for using a galactose donor and a galactose acceptor to detect cancer cells in mammalian tissue or body fluids [3].

DISCLOSURE OF THE INVENTION

This invention comprises a method of using plant lectins to kill cancerous cells that contain abnormally high quantities of galactose moieties on their plasma membranes, such as bladder carcinoma cells.

Research by the Applicants using $RCA_I$ and $BSL_I$ attached to fluorescent markers indicates that certain cancerous cells contain abnormally high levels of β-galactose moieties on their plasma membranes. $RCA_I$ has a high affinity for such moieties; this indicates that the β-galactose moieties on bladder carcinoma cells are accessible and not encrypted. This research was intended to provide means for detecting cancer cells. Surprisingly, $RCA_I$ was also found to severely weaken certain types of cancerous cells. This effect was not expected, and its occurrence substantially disrupted and required a major alteration of the planned program of research.

Weakening of cancer cells by $RCA_I$ is sufficient to kill substantial numbers of cancerous cells. In addition, the weakening effect can serve to fatally damage certain cancerous cells which are subjected to certain types of stress. For example, during urination, bladder cells are subjected to substantial stresses which may be sufficient to kill cancerous cells that have been weakened by $RCA_I$.

In addition, it is possible to bond lectins to certain other substances which impose stress on cells. Such substances may be cytotoxic or they may catalyze exothermic reactions that create local heating. For example, certain enzymes such as the peroxidases catalyze exothermic reactions that may kill cells that are weakened by lectins.

A major advantage of this invention is that non-cancerous cells, which contain relatively low quantities of galactose moieties on their plasma membranes, are relatively unaffected by this treatment. Therefore, this treatment has major advantages over cancer chemotherapy which uses drugs that are cytotoxic to both cancerous and non-cancerous cells.

This invention is useful as postoperative therapy to kill cancerous cells that remain after a tumor has been surgically removed from an animal or human, or as chemotherapy which may be conducted regardless of whether surgery is performed.

BEST MODE FOR CARRYING OUT THE INVENTION

In one preferred embodiment of this invention, $RCA_I$ is administered to a patient suffering from bladder carcinoma. $RCA_I$ may be administered into a bladder by means of a urethral catheter, hypodermic syringe or other means. It may be administered in lieu of surgery, or after surgical removal of cancerous cells, which may be accomplished by freeze-cutting, cauterization, or other surgical techniques.

In a preferred embodiment of this invention, $RCA_I$ may be attached to a molecule that is cytotoxic. Numerous such drugs exist, including methotrexate, daunomycin, bleomycin, and other drugs which are used in cancer chemotherapy. The attachment may be accomplished by covalent bonding or by noncovalent methods, such as formation of a ligand complex.

In another preferred embodiment of this invention, $RCA_I$ may be attached to a molecule that catalyzes an exothermic reaction. The purpose of this embodiment is to subject a cell, which has been weakened by $RCA_I$, to stress caused by localized heating. One example of this embodiment comprises conjugating $RCA_I$ to a class of enzymes called peroxidases. Such enzymes include horseradish peroxidase (HRP). If this conjugate is administered into a bladder that contains carcinoma cells, the $RCA_I$ will bind to $\beta$-galactose moieties on the cancer cells, and kill or weaken carcinoma cells. A dilute solution of peroxide may be administered into the bladder subsequent to administration of the $RCA_I$-HRP conjugate. The HRP catalyzes the transfer of an oxygen atom from the peroxide to uric acid, which is present in urine. This is an exothermic reaction which releases a substantial amount of energy in the vicinity of carcinoma cells. Carcinoma cells which have been substantially weakened by the $RCA_I$ are killed by the localized heating.

It is possible to insert one or more molecules between $RCA_I$ and an enzyme or cytotoxic molecule. For example, $RCA_I$ may be bonded to biotin, a B vitamin. This conjugate is commercially available. Horseradish peroxidase may be covalently bonded to avidin, a protein that is present in avian egg white. Biotin and avidin have an affinity for each other, and will bind together to form a ligand complex. Therefore, if $RCA_I$-biotin and HRP-avidin are mixed together, a ligand complex comprising $RCA_I$-biotin-avidin-HRP will be formed. The biotin-avidin complex acts as a "spacer molecule" which can increase the effectiveness of the enzyme or cytotoxic molecule, for example, by reducing steric hindrances.

Other types of cancerous cells are known or believed to contain abnormally high quantities of $\beta$-galactose moieties on their plasma membranes. For example, $RCA_I$ is believed to bind to breast cancer cells, which indicates that $\beta$-galactose moieties on such cells are accessible and are not encrypted. Routine experimentation by a persons skills in the art will indicate which types of cancerous cells are appropriate targets for $RCA_I$, and whether such cells are substantially weakened or lysed by $RCA_I$. Such cells may be treated by the methods of this invention. If it is desired to treat such cancerous cells by a conjugate of $RCA_I$ and a substance that catalyzes an exodermic reaction, it may be necessary to co-administer one or more substrates, such as an oxygen donor and an oxygen acceptor. For example, if peroxidase is used to catalyze a reaction, it may be necessary to co-administer peroxide, which donates the oxygen atom that is transferred by the peroxidase, and an oxygen acceptor, such as ascorbic acid, unless an oxygen acceptor such as uric acid is already present in the cancerous location.

$RCA_I$ is not believed to be the only lectin that is suitable for use with this invention. Other lectins may be identified which specifically bind $\beta$-galactose moieties and which weaken or lyse cancerous cells. Such lectins may be determined through routine experimentation by people skilled in the art.

As used herein, the term "bonding" comprises covalent bonding, ionic bonding, and formation of a ligand complex, and the term "spacer molecule" comprises any molecule, or combination of molecules, that is inserted between a lectin and molecule which is cytotoxic, exothermic, or otherwise therapeutic.

EXAMPLE 1

Lysis of cancerous cells by $RCA_I$

Cancerous cells used were established from human urinary bladder carcinoma taken from a patient at the Massachusetts General Hospital, Boston, Massachusetts. This cell was designated as MGH-Ul. Cells were suspended in a phosphate buffer saline (PBS) solution comprising 0.15 M NaCl, 0.01 M $Na_2HPO_4$, 0.01 M $Na_4$—EDTA, pH adjusted to 6.0 by HCl.

300 ul of MGH-Ul cell suspension (500,000 cells/cc) were placed in a 15 ml plastic conical centrifuge tube. 10 $\mu l$ of $RCA_I$-Biotin (Vector Labs, 3.3 mg/ml) were added to this tube. The tube was incubated for 15 minutes at room temperature with shaking. 10 $\mu l$ of PBS were added to the tube. The solution was incubated for twenty minutes at room temperatue. One ml of Hanker-Yates developer was added to the tube (5 mg Hanker-Yates developer in 10 cc PBS, plus 0.1 ml of 1% $H_2O_2$ in distilled water). The tube was incubated for 10 minutes at room temperature. 13 ml of PBS were added to the tube. The tube was centrifuged for 10 minutes at 1600 g. The supernatant was decanted and discarded. 13 ml of PBS were added, and the tube was centrifuged as before. The supernatant was decanted and discarded. The pellet was resuspended with PBS to a volume of 0.5 ml. Three drops of this solution were placed on a microscope slide. A cover slip was applied and the slide was observed via light microscope.

Visual observation indicated that most of the cells had become cell debris. About 95% of the intact cells were irregular and rough in shape. About 5% of the intact cells appeared relatively smooth and round, the normal shape for MGH-Ul cells.

The foregoing procedure was repeated using $RCA_I$ that was not conjugated to biotin. The results were the same.

EXAMPLE 2

Lytic Effect Of $RCA_I$

A centrifuged pellet of MGH-Ul cells was suspended in 1 ml of PBS in a 15 ml plastic conical centrifuged tube. 20 $\mu l$ Biotinyl-$RCA_I$ was added and the mixture was allowed to incubate at room temperature for 10 minutes. 9 ml of PBS were added to the tube. A second tube was prepared identically, omitting the addition of Biotinyl-$RCA_I$. Both tubes were spun at 1600 g for 5 minutes. The cells in each tube were counted by means of hemocytometer (Clay-Adams, Boston, MA). The cell concentration in the tube that contained RCA$_I$ was approximately 8% of the cell concentration in the control tube.

EXAMPLE 3

Lytic Effect Of RCA$_I$—Horseradish Peroxidase

The procedures of Example 1 were repeated. In addition, ten μl of avidin-HRP (Vector Laboratories, Burlingame, CA, 3.3 mg/ml) were added to the test tube instead of 10 μl of PBS. After the centrifugation was completed, no normal-looking cells were seen; by comparison, about 5% of the intact cells from the tube without HRP looked normal. More cell debris was seen in the tube that contained HRP than in the tube without HRP.

The procedures of Example 2 were repeated. After Biotinyl-RCA$_I$ and PBS were added and the tube was centrifuged for 5 minutes, 20 μl of avidin-HRP was added to the tube. The mixture was incubated at room temperature for 20 minutes, and 9 ml of PBS was added. The tube was centrifuged at 1600 g for 5 minutes. The cell concentration was determined visually and by means of a hemocytometer. The cell concentration in the tube was approximately 1% of the cell concentration in the control tube.

EXAMPLE 4

Inhibition Of RCA$_I$ Lytic Effect By Lactose

MGH-U1 cells were suspended in 1.5 ml of PBS. Eight drops of this cell suspension were placed in each of two 15 ml conical plastic centrifuge tubes. The tubes were centrifuged at 400 g for 10 minutes, and the supernatant was removed with a pipette. Ten drops of PBS without EDTA, pH 7.4 via HCl, were added to one tube. Ten drops of the same solution, with 0.1 M β-lactose, were added to the second tube. Both tubes were incubated for 10 minutes at room temperature. Each tube then received 10 ul of RCA$_I$ (3.3 mg/ml). Immediate cell agglutination was observed in the tube without lactose; no cell agglutination was observed in the tube with lactose. The tubes were shaken and incubated for 10 minutes at room temperature. A sample from each tube was examined by light microscope. Cells from the tube with lactose appeared round, unclumped and healthy. Cells from the tube without lactose appeared ragged and clumped; about 5% of the cells were lysed at this stage.

Both tubes were then centrifuged at 1600 g for 10 minutes. The pellets were resuspended into the supernatants, and samples were examined by light microscope. Cells from the tube with lactose appeared round, unclumped, and healthy looking. Cells from the tube without lactose appeared misshapened, and coated with membranous debris. Approximately 10 to 25% of the cells had been lysed, and a substantial amount of cellular debris was dispersed in the solution.

EXAMPLE 5

Absence of RCA$_I$ Affinity for Non-Cancerous Cells

A 200 ml urine sample donated by a healthy, cancer-free male was mixed with a 150 ml culture that contained cancerous MGH-U1 cells. About 1 ml of PBS and EDTA were added to the mixture, which was then stored at about 4° C. for 3 days. About 30 ml was withdrawn and centrifuged into a pellet, which was resuspended in PBS and EDTA. The suspension was then applied to microscope slides and air-dried, and the cells were affixed to the slides by soaking in acetone for 10 minutes.

10 μl of RCA$_I$-Biotin was mixed with 6 drops of PBS, EDTA, and 1% Tween 80. The mixture was applied to slides, cover slips were applied, and the slides were incubated for 20 minutes at room temperature. The cover slips were removed, and the slides were soaked in 200 ml of PBS and EDTA for 20 minutes, then air dried. 10 μl of Avidin-HRP was mixed with 6 drops of PBS, EDTA, and 1% Tween 80, and applied to the slides in the manner described above. The slides were then incubated with 5 mg Hanker-Yates developer in 10 cc PPS and Tween 80 with 1% $H_2O_2$ in distilled water. The slides were then soaked in PBS for 20 minutes, and cover slips were applied. The slides were observed under light microscopy. The results indicated that the cancerous MGH-U1 cells were stained, while the non-cancerous cells were not stained.

EXAMPLE 6

Therapeutic Effect of RCA$_I$ on Mice

Approximately 12 male nude (athymic) mice with an average weight of about 25 g were injected in the central dorsal area with at least 100,000 cells of MGH-U1 bladder carcinoma in a 0.1 ml solution of PBS. After 1 week, two of the mice were injected with 5 μg each of RCA$_I$ in a 0.1 ml solution of PBS. Those two mice did not develop tumors within a period of about five weeks after cell injection. At this time, they were sacrificed, examined, and found to have no evidence of tumor formation. By contrast, all mice injected with 100,000 or more MGH-U1 cells that did not received RCA$_I$ treatment developed palpable vascularized tumors within two weeks after cell injection.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

REFERENCES

1. See, e.g., R. Lotan et al, *Biochemica et Biophysica Acta*, 559: 329–376 (1979).
2. See Weiser et al, *Proc. Nat. Acad. Sci.* 73: 1319–1322 (1976).
3. See U.S. Pat. No. 4,132,600 (Plotkin et al, 1979).

We claim:

1. A method of treating cancer cells, comprising contacting the cells with a lectin which specifically binds galactose moieties on the surface of the cell membrane thereby weakening the cell membrane; and, thereafter, applying sufficient localized stress within the cell environs to rupture the weakened cell membrane.

2. A method of claim 1 wherein the lectin comprises *Ricinus communis* agglutinin I or *Bandeirae simplicifolia* lectin I.

3. A method of claim 1 wherein the stress is provided by thermal or mechanical energy.

4. A method of treating cancer cells comprising
contacting the cells with a lectin which specifically binds galactose moieties on the surface of the cell membrane, said lectin being bonded to an enzyme which catalyzes an exothermic reaction; and, then, contacting the cells with a substrate for said enzyme whereby the release of heat caused by the ensuing exothermic reaction provides stress sufficient to rupture the cell membrane.

5. A method of claim 4 wherein the lectin is Ricinus communis agglutinin I or Bandeirae simplicifolia lectin I.

6. A method of claim 4 wherein the lectin is bonded to horseradish peroxidase and the substrate is hydrogen peroxide.

7. A method of treating bladder cancer comprising introducing into the bladder a lectin which binds specifically to galactose moieties on the surface of a cell membrane, said lectin being bound to an enzyme which catalyzes an exothermic reaction, and them, introducing into the bladder a substrate for said enzyme.

8. A method of claim 7 wherein the lectin is *Ricinus communis* agglutinin I bound to horseradish peroxidase and the substrate is hydrogen peroxide.

* * * * *

UNITED STATES PATENT AND TRADEMARK OFFICE
CERTIFICATE OF CORRECTION

PATENT NO. : 4,496,539
DATED : January 29, 1985
INVENTOR(S) : Plotkin et al.

It is certified that error appears in the above—identified patent and that said Letters Patent is hereby corrected as shown below:

Column 3, line 59, "persons skills" should be ---person skilled---.

Column 3, line 65, "exodermic" should be ---exothermic---.

Column 4, line 26, "phosphate buffer" should be ---phosphate-buffered---.

Column 6, line 12, "PPS" should be ---PBS---.

Signed and Sealed this

First Day of October 1985

[SEAL]

Attest:

Attesting Officer

DONALD J. QUIGG

Commissioner of Patents and
Trademarks—Designate